(12) United States Patent
Sala

(10) Patent No.: US 8,217,170 B2
(45) Date of Patent: Jul. 10, 2012

(54) PROCESS FOR THE PREPARATION OF TERTIARY N-ALLYL STERICALLY HINDERED AMINES

(75) Inventor: Massimiliano Sala, Castelnuovo Rangone (IT)

(73) Assignee: BASF SE, Ludwigshafen (DE)

( * ) Notice: Subject to any disclaimer, the term of this patent is extended or adjusted under 35 U.S.C. 154(b) by 343 days.

(21) Appl. No.: 12/515,414

(22) PCT Filed: Nov. 14, 2007

(86) PCT No.: PCT/EP2007/062321
§ 371 (c)(1),
(2), (4) Date: Nov. 16, 2009

(87) PCT Pub. No.: WO2008/061923
PCT Pub. Date: May 29, 2008

(65) Prior Publication Data
US 2010/0087639 A1    Apr. 8, 2010

(30) Foreign Application Priority Data
Nov. 23, 2006   (EP) ..................................... 06124615

(51) Int. Cl.
*C07D 401/14*   (2006.01)
(52) U.S. Cl. ......... 544/198; 546/184; 546/186; 546/242
(58) Field of Classification Search .................. 546/184, 546/186, 242; 544/198
See application file for complete search history.

(56) References Cited

U.S. PATENT DOCUMENTS

| 4,014,887 A | 3/1977 | Randell et al. | |
|---|---|---|---|
| 4,141,883 A | 2/1979 | Soma et al. | |
| 4,898,946 A * | 2/1990 | Costanzi et al. | 546/216 |
| 6,420,462 B1 * | 7/2002 | Zedda et al. | 524/100 |

OTHER PUBLICATIONS

Muzart, J. Tetrahedron 61 (2005) 4179-4212.*
Y. Masuyama et al., Chemistry Letters, (1995), pp. 1121-1122.
B. Walchuk et al, Polymer Preprints, vol. 39, No. 1, Mar. 1998, pp. 296-297.
G. Bitsi et al., Journal of Organometallic Chemistry, vol. 373, (1989), pp. 343-352.

* cited by examiner

*Primary Examiner* — Venkataraman Balasubramanian
(74) *Attorney, Agent, or Firm* — Tyler A. Stevenson

(57) ABSTRACT

The instant invention discloses a process for the preparation of compounds of the formula (I), wherein the general symbols are as defined in claim 1, which process comprises reacting a sterically hindered amine of the formula (II), wherein the general symbols are as defined in claim 1, with a compound of the formula (III) wherein the general symbols are as defined in claim 1, in the presence of a catalyst. The compounds of the formula (I) are useful as stabilizers for protecting organic materials, in particular synthetic polymers, reprographic materials or coating materials against oxidative, thermal or light-induced degradation.

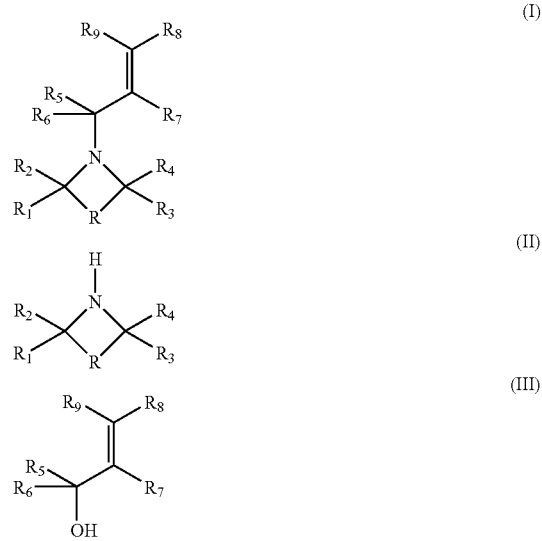

10 Claims, No Drawings

PROCESS FOR THE PREPARATION OF TERTIARY N-ALLYL STERICALLY HINDERED AMINES

The present invention relates to an improved process for the preparation of tertiary N-allyl sterically hindered amines which are suitable for stabilizing organic materials against oxidative, thermal or light-induced degradation.

Sterically hindered amine light stabilizers which are N-allyl substituted are prepared from the corresponding sterically hindered secondary amines by alkylation with allyl halides in the presence of bases at high temperature.

The cost of allyl halides is increasing constantly and has a high impact on the production cost of these N-allyl stabilizers. A further disadvantage of using allyl halides is the fact that this synthetic route generates salts as side products which are environmentally critical and which have to be removed.

A halide free process for the preparation of tertiary N-allyl sterically hindered amines from the corresponding sterically hindered secondary amines is therefore highly desirable.

It has now been found that sterically hindered amines can be reacted with allyl alcohols in the present of a catalyst and carbon dioxide as activator to form the desired N-allyl sterically hindered amines.

The present invention therefore relates to an improved process for the preparation of compounds of the formula I

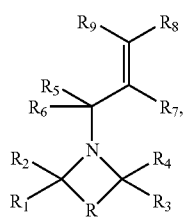

(I)

wherein the linking group R forms, together with the carbon atoms it is directly connected to and the nitrogen atom, a substituted 5-, 6- or 7-membered cyclic ring structure, $R_1$, $R_2$, $R_3$ and $R_4$, independently of each other, are $C_1$-$C_8$alkyl or $C_1$-$C_5$hydroxyalkyl, or $R_1$ and $R_2$ together with the carbon atom they are attached to are $C_5$-$C_{12}$cycloalkyl, or $R_3$ and $R_4$ together with the carbon atom they are attached to are $C_5$-$C_{12}$cycloalkyl, $R_5$, $R_6$, $R_7$, $R_8$ and $R_9$, independently of each other, are hydrogen, $C_1$-$C_8$alkyl, $C_2$-$C_8$alkenyl, unsubstituted or with $C_1$-$C_4$alkyl, $C_1$-$C_4$alkoxy or halogen substituted $C_5$-$C_{12}$aryl; $C_1$-$C_4$haloalkyl, cyano, nitro, halogen or —$COOR_{10}$; and $R_7$ and $R_8$ together may also form a chemical bond, $R_{10}$ is $C_1$-$C_{12}$alkyl, $C_5$-$C_{12}$cycloalkyl, $C_7$-$C_9$phenylalkyl or phenyl, which process comprises reacting a compound of the formula II

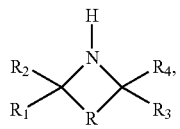

(II)

wherein R, $R_1$, $R_2$, $R_3$ and $R_4$ are as defined above, with a compound of the formula III

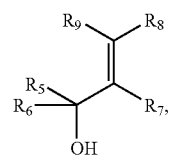

(III)

wherein $R_5$, $R_6$, $R_7$, $R_8$ and $R_9$ are as defined above, in the presence of a catalyst.

Alkyl having up to 12 carbon atoms is a branched or unbranched radical, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl or 1,1,3,3,5,5-hexamethylhexyl.

Hydroxyalkyl having up to 5 carbon atoms is a branched or unbranched radical which contains preferably 1 to 3, in particular 1 or 2, hydroxyl groups, such as, for example, 1-hydroxymethyl, 1-hydroxyethyl, 1-hydroxypropyl, 1-hydroxybutyl, 1-hydroxybutyl, 2-hydroxyethyl, 2-hydroxypropyl, 2-hydroxybutyl, 2-hydroxybutyl, 2-hydroxypropyl or 3-hydroxybutyl.

$C_5$-$C_{12}$cycloalkyl is, for example, cyclopentyl, cyclohexyl, cycloheptyl, cyclooctyl, cyclononyl, cyclodecyl, cycloundecyl or cyclododecyl.

Alkenyl having 2 to 8 carbon atoms is a branched or unbranched radical such as, for example, vinyl, propenyl, 2-butenyl, 3-butenyl, isobutenyl, n-2,4-pentadienyl, 3-methyl-2-butenyl or n-2-octenyl.

Aryl stands for a group obeying the Debye-Hueckel rule; preferred as $C_5$-$C_{12}$aryl are phenyl and naphthyl.

Halogen is for example fluoro, chloro, bromo or iodo.

$C_7$-$C_9$Phenylalkyl is, for example, benzyl, α-methylbenzyl, α,α-dimethylbenzyl or 2-phenylethyl. Preference is given to benzyl and α,α-dimethylbenzyl.

Alkoxy having up to 4 carbon atoms is a branched or unbranched radical, for example methoxy, ethoxy, propoxy, isopropoxy, n-butoxy or isobutoxy.

Of interest is a process for the preparation of compounds of the formula I wherein $R_1$, $R_2$, $R_3$ and $R_4$ are methyl.

Also of interest is a process for the preparation of compounds of the formula I wherein $R_5$, $R_6$, $R_7$, $R_8$ and $R_9$ are hydrogen.

Of very special interest is a process for the preparation of compounds of the formula I, wherein R is

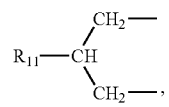

and $R_{11}$ is nitrogen which is attached to triazine ring.

Preferred is a process for the preparation of compounds of the formula I, wherein R is

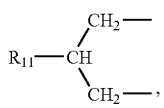

$R_1$, $R_2$, $R_3$ and $R_4$ are methyl,
$R_5$, $R_6$, $R_7$, $R_8$ and $R_9$ are hydrogen, and
$R_{11}$ is nitrogen which is attached to triazine ring.

Also preferred is a process for the preparation of compounds of the formula I, wherein the compounds of the formula I are part of monomeric, oligomeric or polymeric sterically hindered amine light stabilizers.

Preferably, the compound of the formula III is used in equimolar to 100 fold excess, for example 1 to 50 fold excess, preferably, 1 to 20 fold excess, typically 1 to 4 fold excess, with respect to each unit of secondary sterically hindered amine of the formula II.

Preferably the catalyst is a metal catalyst. Of interest are metal catalysts selected from the group consisting of palladium, rhodium, ruthenium, osmium, copper, nickel, manganese, iron and cobalt catalysts.

Preferably, the catalyst is used in the process for the preparation of the compounds of the formula I in an amount of from 0.01 to 30 mol %, preferably 0.01 to 20 mol %, typically 0.1 to 10 mol %, with respect to each unit of secondary sterically hindered amine of the formula II.

Of interest is also a process for the preparation of the compounds of the formula I wherein the catalyst is a metal catalyst containing phosphine ligands.

Examples for phosphines are compounds of the formula IV $$P(Q)_3 \qquad (IV)$$

wherein Q is the same or different and is for example alkyl having 1 to 10 carbons, cycloalkyl having 4 to 10 carbons and/or aryl having 6 to 10 carbons, examples of which are methyl, butyl, cyclohexyl, phenyl, tolyl. Preferably at least one is aryl and most preferably, the ligand is triaryl.

Examples of suitable ligands having the aforementioned structure are the following: trimethylphosphine, tricyclohexylphosphine, tris(m-sulfonatophenyl)phosphine (TPPTS), triphenylphosphine, 2,2'-bis(diphenylphosphino)-1,1'-binaphthalene (BINAP). Preferred ligand is triphenylphosphine.

Preferably, the quantity of the ligand is from 1 to 10 moles per atom of the metal. An especially preferred ligand/atom metal ratio is from 2 to 6.

Of special interest is a process for the preparation of compounds of the formula I wherein the catalyst is palladium (tetrakistriphenylphosphine).

The process for the preparation of compounds of the formula I may comprise additionally a solvent and/or a base.

Useful solvents for the instant process are for example saturated and aromatic hydrocarbons, ketones, esters, water or alcohols or mixtures thereof. Preferably, the solvent may be the compound of the formula III (allyl alcohol). Examples of especially preferred organic solvents are toluene, xylene, acetone, methanol or ethyl acetate.

The bases are inorganic or organic in nature. Bases of special interest are for example sodium carbonate, potassium carbonate, sodium hydroxide, triethylamine or pyridine.

The reaction temperature in the instant process for the preparation of the compounds of the formula I is for example between 10 and 180° C., preferably between 20 and 140° C., and pressures of 1 to 30 atmospheres absolute, preferably of 1 to 15 atmospheres absolute.

Of very special interest is also a process for the preparation of compounds of the formula I wherein additionally carbon dioxide or another inert gas or a mixture thereof is present. Examples of inert gases are for example nitrogen or argon. Preferably, mixtures of inert gases are used comprising carbon dioxide and nitrogen.

The following Examples illustrate the invention further. Parts or percentages relate to weight.

EXAMPLE 1

Preparation of Compound 101 Starting from Compound A

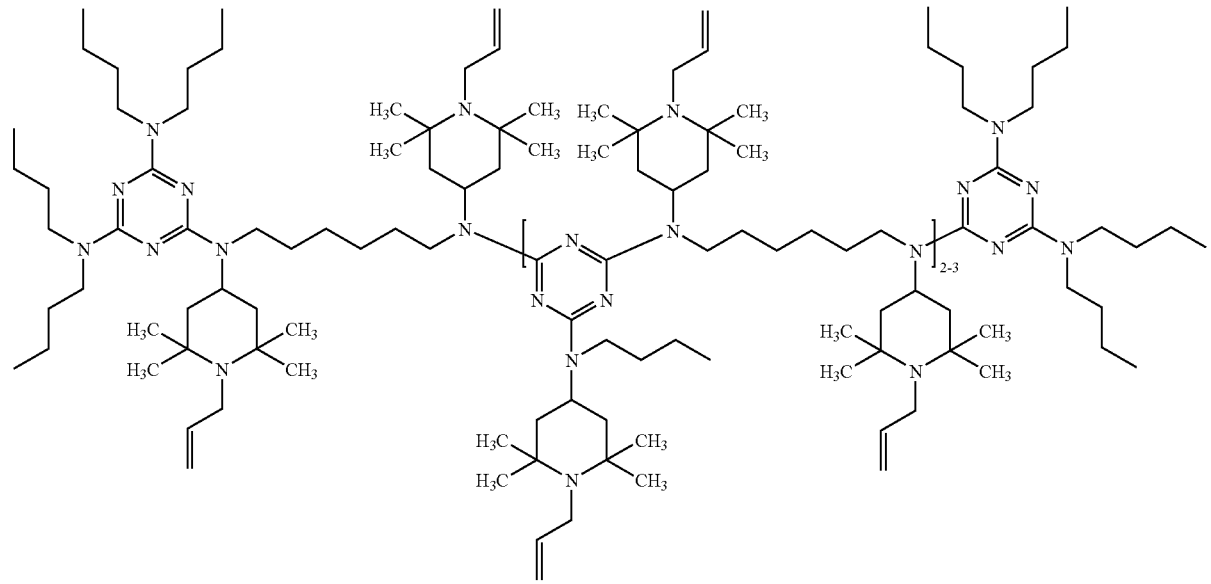

(101)

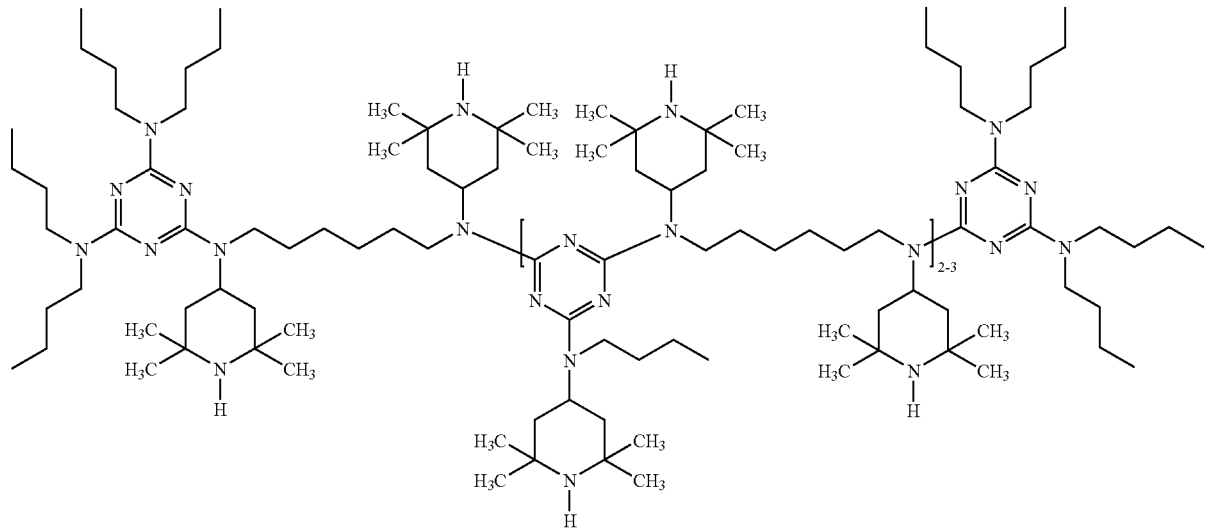

(A)

In a round-bottom flask equipped with mechanical stirrer, condenser and a rubber balloon containing $CO_2$, 7.0 g (Mw 3889, 23.27 mmol of piperidine units) of compound A [prepared according to Example 1 in U.S. Pat. No. 6,117,995], 2.7 g (46.9 mmol) of allyl alcohol, 0.46 g (0.4 mmol) of palladium(tetrakistriphenylphosphine) and 2.37 g (22.8 mmol) of triethylamine are added to 25 ml of toluene. The mixture is stirred for 22 hours at 50° C. Then, the crude reaction is analyzed by $^1$H-NMR to reveal that 47% of N—H groups of 2,2,6,6-tetramethylpiperidinic units of compound A are converted into the corresponding N-allyl thus forming also compound 101.

EXAMPLE 2

Preparation of Compound 102

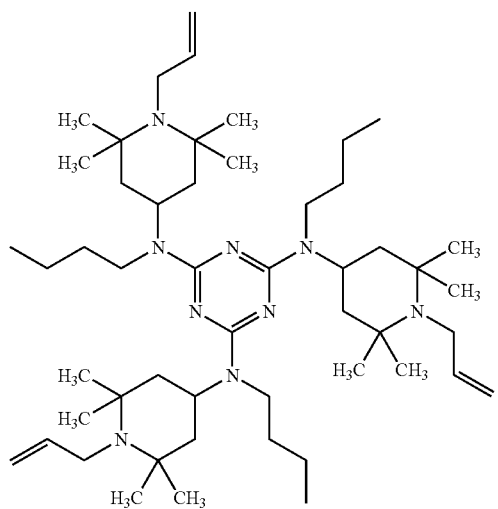

(102)

In an autoclave equipped with mechanical stirrer 7.12 g (10.0 mmol) of 2,4,6-tris(N-n-butyl-N-2,2,6,6-tetramethylpiperidin-4-yl))-1,3,5-triazine, 3.45 g (60 mmol) of allyl alcohol, 0.57 g (0.5 mmol) of palladium(tetrakistriphenylphosphine) are added to 30 ml of acetone. Then, the atmosphere is saturated with $CO_2$ and the reaction mixture is maintained under vigorous stirring for 60 hours at 30° C. Then, the crude reaction is analyzed by $^1$H-NMR to reveal that 70% of N—H groups of 2,2,6,6-tetramethylpiperidinic unit of 2,4,6-tris(N-n-butyl-N-2,2,6,6-tetramethylpiperidin-4-yl)-1,3,5-triazine are converted into the corresponding N-allyl thus forming also compound 102.

EXAMPLE 3

Preparation of Compound 102 (see Formula in Example 2)

In an autoclave equipped with mechanical stirrer 5.00 g (7.0 mmol) of 2,4,6-tris(N-n-butyl-N-2,2,6,6-tetramethylpiperidin-4-yl))-1,3,5-triazine, 4.89 g (84.2 mmol) of allyl alcohol are added to 25 ml of toluene. Then 0.16 g (0.7 mmol) of palladium acetate and 0.37 g (1.4 mmol) of triphenylphosphine are successively added to the solution maintained under nitrogen atmosphere. The reaction mixture is left to react under vigorous stirring for 16 hours at 80° C. Then, the crude reaction is analyzed by $^1$H-NMR to reveal that 19% of N—H groups of 2,2,6,6-tetramethylpiperidinic unit of 2,4,6-tris(N-n-butyl-N-2,2,6,6-tetramethylpiperidin-4-yl)-1,3,5-triazine are converted into the corresponding N-allyl thus forming also compound 102.

What is claimed is:
1. A process for the preparation of a sterically hindered amine compound of formula I

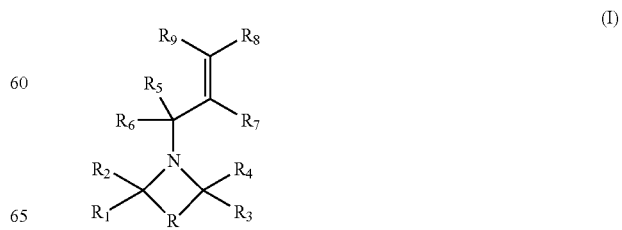

(I)

wherein the linking group R is

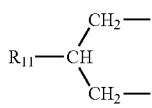

where

R$_{11}$ is nitrogen which is attached to a triazine ring,

R$_1$, R$_2$, R$_3$ and R$_4$, independently of each other, are C$_1$-C$_8$alkyl or C$_1$-C$_5$hydroxyalkyl, or R$_1$ and R$_2$ together with the carbon atom they are attached to are C$_5$-C$_{12}$cycloalkyl, or R$_3$ and R$_4$ together with the carbon atom they are attached to are C$_5$-C$_{12}$cycloalkyl and R$_5$, R$_6$, R$_7$, R$_8$ and R$_9$, independently of each other, are hydrogen, C$_1$-C$_8$alkyl, C$_2$-C$_8$alkenyl, unsubstituted or C$_1$-C$_4$alkyl, C$_1$-C$_4$alkoxy or halogen substituted C$_5$-C$_{12}$aryl; C$_1$-C$_4$haloalkyl, cyano, nitro, halogen or —COOR$_{10}$; or R$_7$ and R$_8$ together may form a chemical bond, where R$_{10}$ is C$_1$-C$_{12}$alkyl, C$_5$-C$_{12}$cycloalkyl, C$_7$-C$_9$phenylalkyl or phenyl, which process comprises reacting a secondary sterically hindered amine compound of formula II

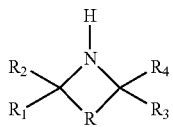

wherein R, R$_1$, R$_2$, R$_3$ and R$_4$ are as defined above, with a compound of formula III

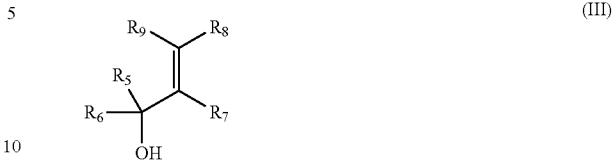

wherein R$_5$, R$_6$, R$_7$, R$_8$ and R$_9$ are as defined above, in the presence of palladium(tetrakistriphenylphosphine) catalyst.

2. A process according to claim 1, wherein R$_1$, R$_2$, R$_3$ and R$_4$ are methyl.

3. A process according to claim 1, wherein R$_5$, R$_6$, R$_7$, R$_8$ and R$_9$ are hydrogen.

4. A process according to claim 1, wherein
R$_1$, R$_2$, R$_3$ and R$_4$ are methyl and
R$_5$, R$_6$, R$_7$, R$_8$ and R$_9$ are hydrogen.

5. A process according to claim 1, wherein the compounds of formula I are monomeric, oligomeric or polymeric sterically hindered amine light stabilizers.

6. A process according to claim 1, wherein the compound of formula III is used in an equimolar amount to 100 fold excess with respect to each unit of secondary sterically hindered amine of formula II.

7. A process according to claim 1, wherein the catalyst is used in an amount of 0.01 to 30 mol % with respect to each unit of the secondary sterically hindered amine of formula II.

8. A process according to claim 1, wherein additionally a solvent is present.

9. A process according to claim 1, wherein additionally a base is present.

10. A process according to claim 1, wherein additionally carbon dioxide or another inert gas or a mixture thereof is present.

* * * * *